United States Patent [19]

Fabbri et al.

[11] Patent Number: 5,017,557

[45] Date of Patent: May 21, 1991

[54] TREATMENT OF INFERTILITY WITH SOMATOTROPHIN RELEASING FACTOR

[75] Inventors: Andrea Fabbri; Costanzo Moretti; Laura Forni, all of Rome, Italy

[73] Assignee: Industria Farmaceutica Serono S.p.A., Rome, Italy

[21] Appl. No.: 216,805

[22] Filed: Jul. 8, 1988

[30] Foreign Application Priority Data

Jul. 24, 1987 [IT] Italy .................. 48222 A/87
Apr. 26, 1988 [IT] Italy .................. 47887 A/88

[51] Int. Cl.$^5$ .................. A61K 37/24; A61K 37/36
[52] U.S. Cl. .................. 514/12; 514/2; 514/21
[58] Field of Search .................. 514/12, 21, 2, 800

[56] References Cited

U.S. PATENT DOCUMENTS 4,910,215 3/1990 Müller .................. 514/401

OTHER PUBLICATIONS

Stedman's Medical Dictionary, 24th ed., Williams and Wilkins, Baltimore, 1982, p. 601.
Arce, Nemoendocrinology, 52/51/90:119, 1990, Poster 3.50 of 2nd Int'l Cong. of Neuroendocrinology held Jun. 24-29, 1990.
Valcari, Clin. Endocrinol., 29:309, 1988.

Primary Examiner—F. T. Moezie
Attorney, Agent, or Firm—Stephan P. Williams

[57] ABSTRACT

The use of somatotrophin releasing factor (GRF) is disclosed for the treatment of infertility in females and males. Also disclosed for such treatment is the use of somatotrophin releasing factor along with gonadotrophins, particularly follicle stimulating hormone (FSH) or preparations containing FSH. Pharmaceutical preparations containing somatotrophin releasing factor, including preparations containing both somatotrophin releasing factor and follicle stimulating hormone, are also disclosed.

19 Claims, No Drawings

TREATMENT OF INFERTILITY WITH SOMATOTROPHIN RELEASING FACTOR

SUMMARY OF THE INVENTION

The invention refers to the new use of GRF (Somatotrophin releasing factor), alone or in combination with the follicle-stimulating hormone, in the treatment of infertility.

The present invention relates to the treatment of male and female infertility using a Somatotrophin releasing factor, alone or in combination with the follicle-stimulating hormone, or to the relevant pharmaceutical preparations.

The efficacy of the Follicle Stimulating Hormone (FSH) in the induction of Progesterone synthesis by ovarian granulosa cells is well known. The acquisition of the capacity to synthetize progesterone by such cells, in turn, determines the completion of the maturation of the oocyte, for correct follicle growth and the normal functioning of corpus luteum.

Therapy with FSH and Chorionic Gonadotrophin has become the main treatment of anovulatory sterility due to insufficient endogenous secretion of gonadotrophins. FSH can be administered as Menotrophin or HMG (Human Menopausal Gonadotrophin), a preparation containing the same number of units of biological activity (I.U.) of the hormones FSH and LH (=Luteinizing Hormone), or as Urofollitrophin, a preparation containing FSH and insignificant quantities of LH.

The applicant markets such preparations under the names Pergonal ® and Metrodin ®, respectively.

Due to the demonstrated efficacy of gonadotrophins on the Sertoli cells, that is, the male equivalent of the ovarian granulosa cells, the same preparations are also used for the treatment of male infertility.

As stated above, while treatment with gonadotrophins has become the treatment of choice in female and male infertility, there are some clinical conditions in which this kind of treatment is not efficacious.

Studies carried out in normal subjects during the menstrual cycle have demonstrated that the intravenous administration of GRF produces an increase in serum levels of HGH and Sm-C but not of prolactin, LH or FSH (Evans W. S., et al.—Effects of human pancreatic growth-hormone-releasing factor-40 on serum growth hormone, prolactin, luteinizing hormone, follicle-stimulating hormone and somatomedin-C concentrations in normal women throughout the menstrual cycle. *J. Clin. Endoc. Metab.* 59: 1006, 1984).

It has also been demonstrated that Sm-C in nanomolar concentrations enhances FSH capacity in inducing synthesis of progesterone by cultured rat granulosa cells (Adashi E. Y., and others—Somatomedin-C synergizes with follicle-stimulating hormone in the acquisition of progestin biosynthetic capacity by cultured rat granulosa cells. *Endocrinology* 116:2135, 1985).

Not all the growth factors carry out the same kind of action.

It is known, for example, that EGF (=Epidermal Growth Factor) has an inhibitory effect on FSH-induced cyclic AMP production, and therefore on ovarian granulosa cells differentiation. Another growth factor, TGF-beta (=Transforming Growth Factor-beta) modulates the effect of FSH and EGF during the differentiation process of the same cells (Pei Feng, and others-Transforming Growth Factor beta regulates the Inhibitory Actions of Epidermal Growth Factor during Granulosa Cell Differentiation—*J. Biol. Chem.* 261(30), 14167, 1986).

In conclusion, it is evident that growth factors have a regulatory effect on the above mentioned processes of cell differentiation and interact with FSH at the cell target level of this gonadotrophin. Nevertheless, their mechanism of action and relative synergism have not yet been explained.

It has now been discovered that GRF is capable of interacting with the ovarian follicle-genesis and spermatogenesis regulatory mechanisms and with the maturation of spermatozoa.

It has also been discovered that GRF increases the in-vivo effect of gonadotrophins on the gonads.

Therefore, the main object of the present invention is the therapeutic use of GRF in treatment of cases of female and male infertility. A further object of this invention consists in a combined therapy of GRF and gonadotrophins, applicable whenever it is desirable or necessary to increase the effect of gonadotrophins on the gonads.

Other aims and advantages of the present invention will result from the following detailed description.

Abundant literature on GRF exists. (See, for example, Guillemin et al. *Science* 218, 585, 1982; Esch et al., *J. Biol. Chem.* 258,1806, 1983).

Various forms of GRF have been purified and their aminoacid sequence has been determined. GRF-44 contains the complete aminoacid sequence of GRF-40 and is extended at the carboxylic terminal by four aminoacids.

GRF-40, in turn, contains the complete aminoacid sequence of GRF-37 and is extended at the carboxylic terminal by three aminoacids.

It has been shown that peptide GRF-29 is also biologically active (J. Rivier et al., *Nature*, 300, 276-8, 1982).

It has also been demonstrated that GRF-NH$_2$-44 is the mature hormone and that GRF 40, 37 and 29 are all biologically active fragments.

It has further been demonstrated that the various GRFs react both at the level of synthesis and at the level of release of the growth hormone by the hypophysis (Brazeau et al., *Proc. Nat. Acad. Sci.* 79, 7909, 1982; Baringa et al., *Nature* 306, 84, 1983).

GRF can be administered by the intravenous, intramuscular or subcutaneous routes. Other routes of administration, capable of providing the necessary hematic levels of GRF, are included in the present invention.

In the clinical trials reported below, GRF-29 was used in the form of lyophilized ampoules containing 100 or 150 micrograms (mcg) of GRF and 10 milligrams (mg) of mannitol as excipient. The lyophilized substance, dissolved in 2 ml of physiologic saline, was administered by the intravenous route.

The pharmaceutical production of GRF ampoules was carried out by using traditional methods and does not present any particular difficulty.

IN-VITRO STUDIES

Studies have been carried out to determine immunoreactivity to GRF in human seminal and follicular fluids and in the supernatant of isolated Leydig rat cells; furthermore, binding sites for GRF have been identified in isolated Sertoli rat cells.

1. MATERIALS AND METHODS

Follicular Fluid (F.F.)

Follicular fluid was obtained by means of aspiration of the follicles during the laparoscopy carried out under the GIFT or the FIVET programme. The follicular fluid was immediately centrifuged for 15 minutes at 2000 rpm to remove cells and cell fragments, and the supernatant was frozen at −20° C., until its extraction for the GRF dosage.

Seminal Fluid (S.F.)

Seminal fluid was collected from healthy volunteers, ranging in age from 24 to 36, by means of masturbation after 2–5 days of sexual abstinence. After collection, the seminal fluid was kept at room temperature for about 20 minutes until the coagulum liquified and then it was centrifuged for 15 minutes at 1500 rpm to remove spermatozoa and other cellular species. The supernatant was diluted 1:1 with 0.5M acetic acid solution, boiled for 15 minutes and centrifuged for 10 minutes at 1000 rpm. The supernatants were frozen at −20° C.

Leydig Rat Cells Supernatants

Sprague Dawley adult rats aged 50 days were sacrificed, and their testicles removed, decapsulated and placed in a culture medium (Earle) containing 0.025% of collagenase.

After 15–20 minutes of incubation at 34° C. under stirring, the scattered cells were separated from the tubules, centrifuged and replaced in a culture medium containing 0.025% of collagenase.

After three hours of incubation, the supernatant was separated and frozen at −20° C.

Extraction procedure

The samples prepared as described above were thawed and passed through octadodecasililsilice columns (Sep-Pak C18, Waters), activated with 90% methanol and 0,1% BSA; the material was eluted with 90% methanol in 1% HCOOH and subsequently dried under a nitrogen flow at room temperature. Recovery of labelled GRF as extracted by this method is 70%.

The dried residue is reconstituted in PBS+0,3% BSA, 10 mM EDTA and dosed with the RIA method.

RIA Dosage of GRF

Label used: (3-[I]$^{125}$ iodotyrosil$^{10}$) human GRF-44 (Amersham), specific activity about 2000 Ci/mmol.

Anti-serum: anti-GRF obtained in the rabbit (Amersham) against human GRF-44. Cross-reactivity 100% with GRF-29.

Cold: human GRF-44 (Sigma).

Incubation volume: 24 h at 4° C.

Free separation from ligand: with carbon dextran.

Sensibility of the method: 7,8 pg/tube.

Intra- and inter-dosage variability: 5% and 10% respectively.

Preparation of Sertoli Cells and GRF Binding Conditions

Sertoli cells were isolated from the testicles of 14 day old rats, according to the techniques already decribed (A. Fabbri, et al.—Opiate receptors are present in the rat testis: Identification and localization on Sertoli cells. *Endocrinology* 117: 2544–2546, 1985). Briefly, the procedure consisted in the separation of the tubular compartment from the Leydig cells by means of enzymatic dispersion with collagenase and subsequent treatment of the tubules with trypsin and collagenase. The separated cells were applied to 48 well Costar plates at the concentration of approximately 100,000 cells per well. The cells were allowed to adhere to the bottom of the wells for 24 hours in a metabolic incubator at 34° C., in 95% $O_2$/5% $CO_2$. The cells were then washed and incubated in TC 199 10 mM TRIS medium in the presence of iodine labelled GRF-44 at the concentration of $10^{-11}$M for 60 minutes at 4° C. in the presence or absence of $10^{-6}$M cold (unlabelled) human GRF-44. Then the cells were washed 3 times with PBS+0.5% BSA at 4° C.; the radio-activity bound to the cells was then solubilized with 0.1N NaOH and read in a gammacounter.

2. RESULTS

Immunoreactivity to GRF

Immunoreactivity values for GRF in the examined biological fluids were the following:

Follicular fluid = 60 pg/ml

Seminal fluid = 140 pg/ml

Leydig rat cell supernatant = 100 pg/ml.

Binding Sites on the Sertoli Cells

The results obtained showed the presence of specific binding of GRF to Sertoli cells equal to 2.5 fmoles of peptide/70 mcg of protein (about 40 fmoles/mg of protein).

3. CONCLUSIONS

These results indicate that:

1. immunoreactivity to GRF is present both in human follicular and seminal fluid;
2. immunoreactivity to GRF is present in the supernatant of Leydig rat cells and its binding sites are located on the Sertoli cells of the same animal species.

It can therefore be hypothesised that positive clinical effects on follicle-genesis and spermatogenesis could have been due to a direct action of the peptide at ovarian and testicular level, always considering the possibility of an effect mediated by other growth factors.

CLINICAL STUDIES

Treatment of female infertility

In a clinical study carried out in conformity with the present invention women, both with normal follicle-genesis (as control) and follicle-genesis deficiency were treated.

The study consisted in echographic and hormonal monitoring of follicle-genesis during which the volume of the follicle in maturative growth and the plasma levels of 17-beta estradiol and 17-alpha OH progesterone were recorded.

In the controls with normal follicle-genesis, 2 monitorings of the follicle-genesis were carried out in accordance with the above mentioned procedures: the first verified the basal situation and the second was under administration of GRF-29 at the dosage of 100 or 150 mcg/day i.v. from the 1st to the 7th day of the cycle.

In patients with follicle-genesis deficiency, monitorings of the follicle-genesis were carried out: without any medicinal administration (as control); under administration of GRF-29 at the dosage of 100 or 150 mcg/day i.v. from the 1st to the 7th day of the cycle; under administration of FSH (METRODIN ®) at the dosage of 75 or 150 I.U./day i.m. for 7 days; under the combined administration of FSH+GRF at the above dosage.

Case 1 (C.R.)

Age 21—Normal follicle-genesis—Control. The first cycle of observation (basal) shows the presence of follicular activation and evidence of a dominant follicle between the 14th and the 15th day of the cycle, with ovulation between the 17th and the 18th day.

| Day of cycle | Follicle diameter | 17 beta E2 | 17 alpha OH P |
| --- | --- | --- | --- |
| 1 | absent | 58 | 748 |
| 2 | absent | 62 | 840 |
| 3 | 5 mm | 59 | 790 |
| 4 | 5 mm | 64 | 864 |
| 5 | 5 mm | 71 | 854 |
| 6 | 5 mm | 69 | 843 |
| 7 | 5 mm | 74 | 860 |
| 8 | 5 mm | 78 | 890 |
| 9 | 6 mm | 82 | 910 |
| 10 | 7 mm | 84 | 896 |
| 11 | 7 mm | 86 | 930 |
| 12 | 7 mm | 88 | 915 |
| 13 | 10 mm right | 94 | 913 |
| 14 | 11 mm right | 112 | 980 |
| 15 | 15 mm right | 127 | 1040 |
| 16 | 18 mm right | 224 | 1470 |
| 17 | 20 mm right | 196 | 1560 |
| 18 | DEHISCENCE | 136 | 1680 |

The second cycle of observation, carried out under therapy with GRF-29 (100 mcg/day i.v.), shows the presence of follicular activation and evidence of a dominant follicle between the 13th and the 14th day of the cycle, with ovulation between the 15th and 16th day.

| Day of cycle | Follicle diameter | 17 beta E2 | 17 alpha OH P |
| --- | --- | --- | --- |
| 1 | absent | 43 | 470 |
| 2 | absent | 63 | 440 |
| 3 | absent | 58 | 530 |
| 4 | 5 mm | 51 | 580 |
| 5 | 5 mm | 49 | 550 |
| 6 | 5 mm | 53 | 640 |
| 7 | 5 mm | 48 | 620 |
| 8 | 5 mm | 68 | 613 |
| 9 | 5 mm | 5 | 686 |
| 10 | 7 mm | 74 | 694 |
| 11 | 9 mm | 86 | 769 |
| 12 | 11 mm left | 92 | 680 |
| 13 | 16 mm left | 114 | 860 |
| 14 | 19 mm left | 286 | 960 |
| 15 | 22 mm left | 176 | 1214 |
| 16 | DEHISCENCE | | |

Case 2 (S.A.)
Age 24—Normal follicle-genesis—Control.
Basal observation:

| Day of cycle | Follicle diameter | 17 beta E2 | 17 alpha OH P |
| --- | --- | --- | --- |
| 1 | 5 mm | 57 | 326 |
| 2 | 5 mm | 72 | 382 |
| 3 | 5 mm | 61 | 358 |
| 4 | 5 mm | 76 | 287 |
| 5 | 5 mm | 74 | 269 |
| 6 | 10 mm | 78 | 346 |
| 7 | 10 mm | 73 | 358 |
| 8 | 10 mm | 81 | 425 |
| 9 | 12 mm | 95 | 462 |
| 10 | 13 mm | 103 | 592 |
| 11 | 14 mm | 112 | 588 |
| 12 | 16 mm | 187 | 786 |
| 13 | 18 mm | 135 | 1242 |
| 14 | 20 mm | 106 | 1182 |
| 15 | DEHISCENCE | | |

Cycle of observation under GRF-29 150 mcg/day i.v. from the 1st to the 7th day of the cycle:

| Day of cycle | Follicle diameter | 17 beta E2 | 17 alpha OH P |
| --- | --- | --- | --- |
| 1 | 5 mm | 46 | 282 |
| 2 | 5 mm | 43 | 198 |
| 3 | 5 mm | 48 | 364 |
| 4 | 5 mm | 62 | 372 |
| 5 | 5 mm | 57 | 296 |
| 6 | 5 mm | 68 | 318 |
| 7 | 7 mm | 71 | 351 |
| 8 | 7 mm | 82 | 370 |
| 9 | 10 mm | 84 | 432 |
| 10 | 10 mm | 86 | 445 |
| 11 | 12 mm | 92 | 526 |
| 12 | 14 mm | 114 | 788 |
| 13 | 17 mm | 126 | 1128 |
| 14 | 20 mm | 232 | 1246 |
| 15 | 20 mm | 174 | 1751 |
| 16 | DEHISCENCE | | |

Case 3 (C.A.)
Age 34—Patient.

Four years of primary infertility due to follicle-genesis and ovulatory deficiency. Previous echographic and bio-chemical studies, and inductive therapy with clomiphene citrate+ethynylestradiol and/or gonadotrophins, show the presence of a multi-follicular activation without the possibility of evolution to dominance, but with a tendency to luteinization.

The first cycle of observation showed the absence of echographic signs of activation and follicular dominance and the presence of bio-chemical signs of ovarian activation.

Basal observation:

| Day of cycle | Follicle diameter | 17 beta E2 | 17 alpha OH P |
| --- | --- | --- | --- |
| 1 | absent | 74 | 140 |
| 2 | absent | 60 | 176 |
| 3 | absent | 48 | 103 |
| 4 | absent | 61 | 118 |
| 5 | absent | 42 | 123 |
| 6 | absent | 64 | 146 |
| 7 | absent | 96 | 191 |
| 8 | absent | 98 | 178 |
| 9 | absent | 120 | 196 |
| 10 | absent | 137 | 436 |
| 11 | absent | 162 | 764 |
| 12 | absent | 139 | 836 |
| 13 | absent | 87 | 578 |
| 14 | absent | 42 | 798 |
| 15 | absent | 57 | 1032 |
| 16 | absent | 60 | 2263 |
| 17 | absent | 64 | 2023 |
| 18 | absent | 96 | 876 |
| 19 | absent | 71 | 732 |
| 20 | absent | 42 | 876 |
| 21 | absent | 48 | 742 |
| 22 | absent | 38 | 936 |
| 23 | absent | 65 | 878 |
| 24 | absent | 72 | 804 |
| 25 | absent | 66 | 972 |

Menstrual flow occurred spontaneously on the 35th day of the cycle.

The second cycle of study, carried out under administration of GRF-29 (150 mcg/day i.v.), shows the presence of follicular activation, dominance and dehiscence. Taking into account the dimensions reached by the follicle, it may not be excluded that the disappearance of echographic observation after the 16th day of cycle could be due to involution. Bio-chemical data testify the presence of ovulation in this cycle of observations.

| Day of cycle | Follicle diameter | 17 beta E2 | 17 alpha OH P |
|---|---|---|---|
| 1 | absent | 21 | 426 |
| 2 | absent | 24 | 386 |
| 3 | 5 mm | 78 | 147 |
| 4 | 5 mm | 42 | 220 |
| 5 | 7 mm | 60 | 338 |
| 6 | 7 mm | 30 | 470 |
| 7 | 7 mm | 72 | 476 |
| 8 | 7 mm | 81 | 512 |
| 9 | 7 mm | 24 | 338 |
| 10 | 11 mm | 86 | 780 |
| 11 | 11 mm | 144 | 764 |
| 12 | 11 mm | 198 | 940 |
| 13 | 12 mm | 176 | 912 |
| 14 | 15 mm | 166 | 560 |
| 15 | 16 mm | 144 | 1215 |
| 16 | 18 mm | 136 | 2131 |
| 17 | DEHISCENCE | | |

The third cycle of study was carried out under administration of FSH (Metrodin) at the dosage of 150 I.U. from the 1st to the 7th day of the cycle. In this case echographic and bio-chemical signs of ovarian activation without follicular dominance were recorded.

| Day of cycle | Follicle diameter | 17 beta E2 | 17 alpha OH P |
|---|---|---|---|
| 1 | absent | 42 | 161 |
| 2 | absent | 54 | 191 |
| 3 | 5 mm | 58 | 176 |
| 4 | 5 mm | 52 | 182 |
| 5 | 5 mm | 87 | 196 |
| 6 | 5 mm | 132 | 212 |
| 7 | 5 mm | 102 | 232 |
| 8 | 5 mm | 112 | 312 |
| 9 | 5 mm | 114 | 264 |
| 10 | 5 mm | 136 | 287 |
| 11 | 5 mm | 102 | 380 |
| 12 | 5 mm | 164 | 412 |
| 13 | 5 mm | 198 | 397 |
| 14 | 5 mm | 86 | 514 |
| 15 | 5 mm | 78 | 498 |
| 16 | 5 mm | 36 | 780 |
| 17 | 5 mm | 89 | 960 |
| 18 | 5 mm | 86 | 1020 |
| 19 | 5 mm | 98 | 1120 |
| 20 | 5 mm | 107 | 1814 |
| 21 | 5 mm | 54 | 1718 |
| 22 | 5 mm | 62 | 1920 |
| 23 | 5 mm | 67 | 1470 |
| 24 | 5 mm | 65 | 1296 |
| 25 | 5 mm | 44 | 1540 |

Menstrual flow re-occurred on the 26th day of the cycle.

The 4th cycle of study was carried out under administration of GRF-29 (150 mcg/day i.v.)+Metrodin® (150 I.U./day i.m.) from the 1st to the 7th day of the cycle. During this cycle it was possible to observe ovarian activation, follicular dominance and dehiscence on the 18th day of the cycle.

| Day of cycle | Follicle diameter | 17 beta E2 | 17 alpha OH P |
|---|---|---|---|
| 1 | absent | 52 | 291 |
| 2 | absent | 58 | 276 |
| 3 | absent | 72 | 364 |
| 4 | 5 mm | 78 | 386 |
| 5 | 5 mm | 86 | 355 |
| 6 | 7 mm | 92 | 312 |
| 7 | 7 mm | 112 | 296 |
| 8 | 7 mm | 136 | 416 |
| 9 | 10 mm | 128 | 492 |
| 10 | 10 mm | 182 | 512 |
| 11 | 12 mm | 214 | 980 |
| 12 | 14 mm | 176 | 2050 |
| 13 | 16 mm | 187 | 2986 |
| 14 | 16 mm | 86 | 2250 |
| 15 | 18 mm | 92 | 2322 |
| 16 | 20 mm | 95 | 2435 |
| 17 | 20 mm | 106 | 2679 |
| 18 | DEHISCENCE | | |

Case 4 (F.L.)
Age 28—Patient.

Patient suffering from primary couple sterility due to follicle-genesis deficiency. Previous studies demonstrated the absence of follicular maturation. By carrying out a stimulating therapy with clomiphene citrate or gonadotrophins it was possible in the past to demonstrate the presence of follicle-genesis activation and follicle dominance, not followed, however, by ovulation.

The first cycle of observation, carried out without any therapy, shows the absence of follicular activation and dominance after 25 days of study.

| Day of cycle | Follicle diameter | 17 beta E2 | 17 alpha OH P |
|---|---|---|---|
| 1 | absent | 74 | 670 |
| 2 | absent | 87 | 976 |
| 3 | absent | 79 | 986 |
| 4 | absent | 83 | 890 |
| 5 | absent | 56 | 760 |
| 6 | absent | 78 | 857 |
| 7 | absent | 58 | 912 |
| 8 | absent | 67 | 911 |
| 9 | absent | 73 | 892 |
| 10 | absent | 84 | 695 |
| 11 | absent | 103 | 785 |
| 12 | absent | 97 | 775 |
| 13 | absent | 88 | 875 |
| 14 | absent | 89 | 798 |
| 15 | absent | 99 | 823 |
| 16 | absent | 112 | 811 |
| 17 | absent | 74 | 820 |
| 18 | absent | 86 | 756 |
| 19 | absent | 62 | 810 |
| 20 | absent | 70 | 769 |
| 21 | absent | 66 | 758 |
| 22 | absent | 72 | 814 |
| 23 | absent | 81 | 832 |
| 24 | absent | 58 | 906 |
| 25 | absent | 65 | 876 |

Menstrual flow occurred spontaneously on the 38th day.

The second cycle of study carried out under administration of GRF-29 (100 mcg/day i.v.) demonstrates the absence of ovulation but follicle-genesis was activated.

| Day of cycle | Follicle diameter | 17 beta E2 | 17 alpha OH P |
|---|---|---|---|
| 1 | absent | 54 | 689 |
| 2 | absent | 56 | 740 |
| 3 | absent | 53 | 640 |
| 4 | absent | 64 | 678 |
| 5 | absent | 51 | 721 |
| 6 | absent | 58 | 707 |
| 7 | 5 mm | 53 | 814 |

-continued

| Day of cycle | Follicle diameter | 17 beta E2 | 17 alpha OH P |
|---|---|---|---|
| 8 | 5 mm | 62 | 821 |
| 9 | 5 mm | 60 | 824 |
| 10 | 7 mm | 67 | 811 |
| 11 | 7 mm | 72 | 854 |
| 12 | 7 mm | 69 | 814 |
| 13 | 7 mm | 87 | 863 |
| 14 | 10 mm | 98 | 798 |
| 15 | 10 mm | 92 | 902 |
| 16 | 10 mm | 74 | 904 |
| 17 | 10 mm | 86 | 870 |
| 18 | 10 mm | 94 | 986 |
| 19 | 10 mm | 98 | 965 |
| 20 | 10 mm | 87 | 935 |
| 21 | 10 mm | 83 | 879 |
| 22 | 10 mm | 81 | 954 |
| 23 | 10 mm | 78 | 906 |
| 24 | 10 mm | 90 | 887 |
| 25 | 10 mm | 97 | 808 |

Menstrual flow occurred spontaneously on the 33rd day.

The third cycle of the study was carried out under administration of FSH (Metrodin ®) in ampoules of 75 IU/day i.m. from the 1st to the 7th day of the cycle.

Also in this case ovarian activation was demonstrated but correct follicle-genesis and ovulation were absent.

| Day of cycle | Follicle diameter | 17 beta E2 | 17 alpha OH P |
|---|---|---|---|
| 1 | absent | 55 | 760 |
| 2 | absent | 47 | 789 |
| 3 | absent | 49 | 754 |
| 4 | 5 mm | 60 | 810 |
| 5 | 5 mm | 58 | 796 |
| 6 | 7 mm | 46 | 840 |
| 7 | 7 mm | 65 | 786 |
| 8 | 7 mm | 90 | 441 |
| 9 | 7 mm | 87 | 534 |
| 10 | 7 mm | 88 | 675 |
| 11 | 7 mm | 63 | 632 |
| 12 | 7 mm | 68 | 652 |
| 13 | 7 mm | 66 | 678 |
| 14 | 7 mm | 78 | 691 |
| 15 | 7 mm | 102 | 735 |
| 16 | 7 mm | 96 | 709 |
| 17 | 7 mm | 113 | 809 |
| 18 | 7 mm | 95 | 807 |
| 19 | absent | 104 | 812 |
| 20 | absent | 86 | 811 |

During the evening of the 20th day, menstrual flow re-occurred.

The fourth cycle of study was carried out under administration of GRF-29 100 mcg/day+Metrodin ® 75 IU/day via i.v. e i.m. routes respectively from the 1st to the 7th day of the cycle. During this period of observation it was possible to observe a maturative evolution of the follicle with ovulation between the 18th and the 19th day of the cycle.

| Day of cycle | Follicle diameter | 17 beta E2 | 17 alpha OH P |
|---|---|---|---|
| 1 | absent | 42 | 327 |
| 2 | absent | 43 | 543 |
| 3 | 5 mm | 44 | 436 |
| 4 | 5 mm | 48 | 438 |
| 5 | 5 mm | 42 | 395 |
| 6 | 5 mm | 54 | 540 |
| 7 | 5 mm | 43 | 365 |
| 8 | 9 mm left | 126 | 654 |
| 9 | 9 mm left | 84 | 675 |
| 10 | 12 mm left | 72 | 643 |
| 11 | 13 mm left | 96 | 635 |
| 12 | 16 mm left | 108 | 547 |
| 13 | 16 mm left | 78 | 673 |
| 14 | 19 mm left | 99 | 768 |
| 15 | 20 mm left | 150 | 987 |
| 16 | 22 mm left | 165 | 1237 |
| 17 | 22 mm left | 145 | 1570 |
| 18 | 22 mm left | 126 | 1768 |
| 19 | DEHISCENCE | | |

Case 5 (A.V.)

Age 30—Patient.

This patient was included in the study because of primary couple sterility due to follicle maturation deficiency, anovulation and follicular luteinization. Cycles of stimulating therapy with clomiphene citrate and gonadotrophins had been carried out without resolving the clinical situation.

The first cycle of observation, carried out without any therapy, shows the presence of a delayed ovarian activation, of anovulation and follicular luteinization.

| Day of cycle | Follicle diameter | 17 beta E2 | 17 alpha OH P |
|---|---|---|---|
| 1 | absent | 36 | 219 |
| 2 | absent | 41 | 228 |
| 3 | absent | 32 | 217 |
| 4 | absent | 51 | 307 |
| 5 | absent | 45 | 280 |
| 6 | absent | 38 | 275 |
| 7 | absent | 37 | 298 |
| 8 | 5 mm | 32 | 345 |
| 9 | 5 mm | 48 | 318 |
| 10 | 8 mm | 45 | 321 |
| 11 | 8 mm | 42 | 315 |
| 12 | 8 mm | 46 | 324 |
| 13 | 8 mm | 36 | 322 |
| 14 | 8 mm | 38 | 357 |
| 15 | 12.1 mm right | 87 | 432 |
| 16 | 13 mm right | 125 | 456 |
| 17 | 14.6 mm right | 240 | 483 |
| 18 | 15.9 mm right | 144 | 632 |
| 19 | 20.3 mm right | 222 | 608 |
| 20 | 20 mm right | 162 | 634 |
| 21 | 21 mm right | 96 | 687 |
| 22 | 30.3 mm right | 109 | 623 |

Observations on the 22nd day of the cycle revealed the presence of irregularities in the wall of the dominant follicle, showing inner luteinization echoes. Suspension of monitoring was therefore decided. Menstrual flow re-occurred on the 35th day. An echographic study carried out during the menstrual flow demonstrated the disappearance of the follicular formation.

The second cycle of study was carried out under administration of FSH (Metrodin ®) 75 I.U./day i.m. from the 1st to the 7th day of the cycle. It showed a substantial persistence of the situation observed during the cycle of control, except for more precocious ovarian activation.

| Day of cycle | Follicle diameter | 17 beta E2 | 17 alpha OH P |
|---|---|---|---|
| 1 | absent | 56 | 436 |
| 2 | absent | 58 | 412 |
| 3 | absent | 45 | 408 |
| 4 | absent | 57 | 367 |
| 5 | 6 mm | 52 | 418 |

-continued

| Day of cycle | Follicle diameter | 17 beta E2 | 17 alpha OH P |
|---|---|---|---|
| 6 | 6 mm | 65 | 436 |
| 7 | 8 mm | 60 | 562 |
| 8 | 8 mm | 68 | 652 |
| 9 | 8 mm | 78 | 609 |
| 10 | 12 mm left | 108 | 658 |
| 11 | 12.7 mm left | 125 | 634 |
| 12 | 14 mm left | 234 | 676 |
| 13 | 14.3 mm left | 248 | 657 |
| 14 | 14 mm left | 167 | 768 |
| 15 | 16.5 mm left | 225 | 789 |
| 16 | 17.6 mm left | 161 | 750 |
| 17 | 21.5 mm left | 287 | 806 |
| 18 | 26.8 mm left | 308 | 805 |
| 19 | 26.5 mm left | 237 | 865 |
| 20 | 26.5 mm left | 143 | 906 |
| 21 | 26.3 mm left | 128 | 987 |

Observations on the 21st day of the cycle demonstrated clear inner luteinization-like echoes of the dominant follicle. It was therefore decided to suspend the study. Menstrual flow re-occurred spontaneously on the 26th day of the cycle.

An echographic check carried out during the menstrual flow demonstrated the disappearance of the follicular formation during this cycle.

The third cycle of study was carried out under administration of 100 mcg/day i.v. of GRF-29 + 75 I.U. of FSH (Metrodin ®)/day i.m. from the 1st to the 7th day of the cycle. During this period it was possible to observe a better maturative evolution of the follicle with ovulation between the 16th and 17th day of the cycle.

| Day of cycle | Follicle diameter | 17 beta E2 | 17 alpha OH P |
|---|---|---|---|
| 1 | absent | 36 | 287 |
| 2 | absent | 34 | 280 |
| 3 | absent | 46 | 310 |
| 4 | 6 mm | 48 | 298 |
| 5 | 8 mm | 57 | 346 |
| 6 | 8 mm | 58 | 320 |
| 7 | 8 mm | 50 | 318 |
| 8 | 8 mm | 68 | 457 |
| 9 | 10 mm | 102 | 505 |
| 10 | 12 mm right | 126 | 537 |
| 11 | 14 mm right | 156 | 518 |
| 12 | 16 mm right | 142 | 609 |
| 13 | 20 mm right | 245 | 1027 |
| 14 | 21 mm right | 287 | 1124 |
| 15 | 21 mm right | 157 | 1245 |
| 16 | 21 mm right | 134 | 1347 |
| 17 | DEHISCENCE | | |

Menstrual flow re-occurred during the 29th day of the cycle.

Case 6 (C.P.)
Age 32—Patient.

Eight years of primary sterility. Diagnosis of micropolycistic ovary.

Absence of follicle-genesis activation, also under gonadotrophin induction. The patient under observation had been ovariectomized on the left side.

During the first cycle of observation, without any therapy, it was possible to observe echographic, but not bio-chemical, signs of ovarian activation and absence of follicular dominance.

| Day of cycle | Follicle diameter | 17 beta E2 | 17 alpha OH P |
|---|---|---|---|
| 1 | absent | 36 | 402 |
| 3 | absent | 12 | 386 |
| 4 | absent | 47 | 414 |
| 5 | absent | 72 | 428 |
| 6 | absent | 65 | 472 |
| 7 | absent | 49 | 518 |
| 8 | absent | 58 | 464 |
| 9 | absent | 72 | 532 |
| 10 | 5 mm | 32 | 412 |
| 11 | 5 mm | 38 | 651 |
| 12 | 5 mm | 46 | 646 |
| 13 | 5 mm | 41 | 807 |
| 14 | 5 mm | 71 | 687 |
| 15 | 5 mm | 76 | 792 |
| 16 | 5 mm | 49 | 815 |
| 17 | 5 mm | 55 | 842 |
| 18 | 5 mm | 47 | 812 |
| 19 | 5 mm | 49 | 814 |
| 20 | absent | 67 | 1020 |
| 21 | absent | 47 | 819 |
| 22 | absent | 76 | 1112 |
| 23 | absent | 59 | 1046 |
| 24 | absent | 67 | 1100 |
| 25 | absent | 61 | 976 |

Menstrual flow re-occurred spontaneously on the 37th day of the cycle. It was very scarce, and lasted for 2 days (anomalous flow).

The second cycle of observation was carried out under administration of GRF-29 150 mcg/day i.v. from the 1st to the 7th day of the cycle.

A good ovarian activation was observed, followed by the growth of two follicles (within a micropolycistic ovary, as stated above), which presented an involution around the 17th day of the cycle.

| Day of cycle | Follicle diameter | 17 beta E2 | 17 alpha OH P |
|---|---|---|---|
| 1 | absent | 28 | 176 |
| 2 | absent | 48 | 162 |
| 3 | absent | 24 | 382 |
| 4 | 5 mm | 66 | 382 |
| 5 | 5 mm | 78 | 264 |
| 6 | 7 mm | 64 | 147 |
| 7 | 7 mm | 79 | 173 |
| 8 | 9/7 mm | 75 | 186 |
| 9 | 9/8 mm | 78 | 191 |
| 10 | 12/8 mm | 112 | 286 |
| 11 | 12/8 mm | 120 | 367 |
| 12 | 12/8 mm | 136 | 842 |
| 13 | 12/8 mm | 90 | 940 |
| 14 | 12/8 mm | 132 | 913 |
| 15 | 12/8 mm | 138 | 942 |
| 16 | 12 mm | 142 | 1012 |
| 17 | INVOLUTION | 112 | 1067 |

The third cycle of observation was carried out administering Metrodin ® 150 I.U./day i.m. from the 1st to the 7th day of the cycle. Ovarian activation without follicular dominance was echographically and biochemically demonstrated.

| Day of cycle | Follicle diameter | 17 beta E2 | 17 alpha OH P |
|---|---|---|---|
| 1 | absent | 26 | 146 |
| 2 | absent | 28 | 186 |
| 3 | absent | 52 | 216 |
| 4 | absent | 84 | 342 |
| 5 | absent | 56 | 287 |
| 6 | 5 mm | 83 | 298 |
| 7 | 5 mm | 108 | 188 |

| Day of cycle | Follicle diameter | 17 beta E2 | 17 alpha OH P |
|---|---|---|---|
| 8 | 7 mm | 112 | 214 |
| 9 | 7 mm | 138 | 236 |
| 10 | 7 mm | 142 | 287 |
| 11 | 7 mm | 126 | 312 |
| 12 | 7 mm | 116 | 335 |
| 13 | 7 mm | 126 | 288 |
| 14 | 7 mm | 114 | 300 |
| 15 | 7 mm | 118 | 306 |
| 16 | 7 mm | 87 | 297 |
| 17 | 7 mm | 89 | 480 |
| 18 | INVOLUTION | | |

Menstrual flow re-occurred on the 21st day of the cycle.

The fourth observation was carried out administering GRF-29 150 mcg/day i.v.+FSH (Metrodin ®) 150 I.U./day i.m. from the 1st to the 7th day of the cycle. Ovarian activation and follicular dominance were observed, with dehiscence around the 14th day of the cycle.

| Day of cycle | Follicle diameter | 17 beta E2 | 17 alpha OH P |
|---|---|---|---|
| 1 | absent | 26 | 186 |
| 2 | absent | 48 | 296 |
| 3 | absent | 51 | 217 |
| 4 | 5 mm | 76 | 368 |
| 5 | 7 mm | 72 | 412 |
| 6 | 10 mm | 94 | 615 |
| 7 | 10 mm | 102 | 627 |
| 8 | 12 mm | 112 | 742 |
| 9 | 15 mm | 126 | 762 |
| 10 | 16 mm | 138 | 713 |
| 11 | 18 mm | 241 | 816 |
| 12 | 19 mm | 312 | 1120 |
| 13 | 24 mm | 106 | 2400 |
| 14 | DEHISCENCE | | |

Case 7 (E.L.)
Age 37—Patient.

Primary sterility. Absence of ovarian activation, also under administration of high dosages of gonadotrophins. The patient was in secondary amenorrhea and presented a flow only after administration of progesterone. Prior to commencement of the study, menstrual flow was induced by administering Gestone ® 100 mg i.m. The first cycle of observation carried out without any therapy confirmed the absence of echographic and bio-chemical notes on ovarian activation.

| Day of cycle | Follicle diameter | 17 beta E2 | 17 alpha OH P |
|---|---|---|---|
| 1 | absent | 21 | 182 |
| 2 | absent | 28 | 206 |
| 3 | absent | 32 | 164 |
| 4 | absent | 36 | 106 |
| 5 | absent | 31 | 118 |
| 6 | absent | 30 | 146 |
| 7 | absent | 32 | 172 |
| 8 | absent | 34 | 181 |
| 9 | absent | 28 | 196 |
| 10 | absent | 26 | 172 |
| 11 | absent | 21 | 231 |
| 12 | absent | 37 | 356 |
| 13 | absent | 27 | 328 |
| 14 | absent | 35 | 318 |
| 15 | absent | 37 | 372 |
| 16 | absent | 32 | 310 |
| 17 | absent | 30 | 336 |
| 18 | absent | 27 | 327 |
| 19 | absent | 21 | 311 |
| 20 | absent | 26 | 286 |
| 21 | absent | 42 | 215 |
| 22 | absent | 41 | 217 |
| 23 | absent | 38 | 204 |
| 24 | absent | 36 | 236 |
| 25 | absent | 51 | 287 |

On the 45th day of the cycle, the flow not having reoccurred, menstruation was induced by administering Gestone ® 100 mg, i.m.

The second cycle of observation was carried out administering GRF-29 150 mcg/day i.v. from the 1st to the 7th day of the cycle. The presence of echographic notes of ovarian activation, but absence of follicular dominance, was recorded.

| Day of cycle | Follicle diameter | 17 beta E2 | 17 alpha OH P |
|---|---|---|---|
| 1 | absent | 22 | 182 |
| 2 | absent | 23 | 170 |
| 3 | absent | 28 | 212 |
| 4 | absent | 31 | 186 |
| 5 | 5 mm | 36 | 214 |
| 6 | 5 mm | 32 | 182 |
| 7 | 5 mm | 38 | 116 |
| 8 | 7 mm | 30 | 86 |
| 9 | 7 mm | 35 | 214 |
| 10 | 7 mm | 41 | 213 |
| 11 | 7 mm | 32 | 218 |
| 12 | 7 mm | 46 | 236 |
| 13 | 7 mm | 48 | 232 |
| 14 | 7 mm | 51 | 214 |
| 15 | 7 mm | 52 | 182 |
| 16 | INVOLUTION | | |

Menstrual flow was induced by administering Gestone ® 100 mg i.m. on the 45th day of the cycle.

The third cycle of observation was carried out under administration of FSH (Metrodin ®), 150 U.I./day i.m. from the 1st to the 7th day of the cycle. It was possible to observe echographic, but not bio-chemical, signs of ovarian activation and the absence of follicular dominance.

| Day of cycle | Follicle diameter | 17 beta E2 | 17 alpha OH P |
|---|---|---|---|
| 1 | absent | 36 | 112 |
| 2 | absent | 38 | 110 |
| 3 | absent | 46 | 114 |
| 4 | 5 mm | 42 | 162 |
| 5 | 10 mm | 44 | 176 |
| 6 | 10 mm | 48 | 182 |
| 7 | 10 mm | 56 | 196 |
| 8 | 10 mm | 58 | 182 |
| 9 | 10 mm | 64 | 187 |
| 10 | 10 mm | 68 | 173 |
| 11 | 10 mm | 52 | 198 |
| 12 | 10 mm | 56 | 176 |
| 13 | 10 mm | 58 | 187 |
| 14 | 10 mm | 55 | 195 |
| 15 | 10 mm | 46 | 164 |
| 16 | 10 mm | 58 | 156 |
| 17 | 10 mm | 64 | 187 |
| 18 | 10 mm | 72 | 209 |
| 19 | 10 mm | 38 | 212 |
| 20 | 10 mm | 36 | 214 |
| 21 | 10 mm | 28 | 207 |
| 22 | 10 mm | 32 | 286 |
| 23 | 10 mm | 41 | 211 |
| 24 | 10 mm | 32 | 189 |

-continued

| Day of cycle | Follicle diameter | 17 beta E2 | 17 alpha OH P |
|---|---|---|---|
| 25 | 10 mm | 46 | 214 |

Menstrual flow was induced by Gestone ® 100 mg on the 45th day of the cycle.

The fourth cycle of observation was carried out under administration of GRF-29 150 mcg/day i.v.- +Metrodin ® 150 I.U./day i.m. from the 1st to the 7th day of the cycle. It was possible to demonstrate the presence of echographic and bio-chemical signs of follicular activation, dominance and dehiscence.

| Day of cycle | Follicle diameter | 17 beta E2 | 17 alpha OH P |
|---|---|---|---|
| 1 | absent | 31 | 386 |
| 2 | absent | 38 | 394 |
| 3 | absent | 24 | 470 |
| 4 | 5 mm | 34 | 570 |
| 5 | 7 mm | 76 | 640 |
| 6 | 7 mm | 132 | 720 |
| 7 | 7 mm | 139 | 550 |
| 8 | 10 mm | 104 | 420 |
| 9 | 10 mm | 114 | 436 |
| 10 | 10 mm | 188 | 482 |
| 11 | 13 mm | 186 | 560 |
| 12 | 14 mm | 282 | 630 |
| 13 | 16 mm | 308 | 985 |
| 14 | 20 mm | 304 | 1760 |
| 15 | 22 mm | 346 | 3280 |
| 16 | DEHISCENCE | | |

These results demonstrate that administration of GRF-29 during the first phase of the cycle facilitates follicle growth and anticipates, or even induces, ovulation (dehiscence). Furthermore, GRF was capable of coadjuvating, always at follicular level, the effect of FSH in patients with documented anovulation. In these latter cases, treatment with GRF in combination with FSH always caused efficacious follicle growth up until ovulation.

Treatment of male infertility

Patients suffering spermatogenesis deficiencies of various entity with oligospermia or azoospermia, selected according to the criteria of the protocol, were treated for a period of three months with GRF-29 at the dosage of 5 mcg/kg s.c. 3 times a week.

In conformity with the criteria of inclusion in the protocol, all the patients ranged between 25 and 40 years, with normal or above average gonadotrophin levels, and did not present inflammatory processes or other diseases which could have interfered with the seminal parameters. Testicular biopsy showed an arrest of spermatogenesis at spermatid level in the absence of peritubular fibrosis.

The first control was carried out after 45 days from commencement of therapy, and the second control after 3 months. The tests showed an improvement of the seminal parameters, and especially an increase in the number of spermatozoa and their motility, from which the efficacy of the therapy can be deduced.

The above described treatment was carried out by using GRF alone, in consideration of the normal or above average gonadotrophin levels, based on the criteria of inclusion in the protocol. It falls within the scope of the present invention to use GRF to amplify the effect of gonadotrophins in all cases of spermatogenesis deficiency, due to either testicular pathologies or gonadotrophinic secretion deficiency (hypogonadotrophic hypogonadism).

Although the clinical studies reported above were carried out by using FSH as gonadotrophin, it is evident that similar results can be obtained by administering Menotrophin (HMG) or any other preparation containing FSH.

Similarly, the use of GRF-44, or other molecules having analogous activity, in place of the GRF-29 which was used in the above reported clinical studies, can be considered as equivalent.

We claim:

1. A method of treating infertility comprising administering to a patient in need of such treatment a pharmacologically efficacious quantity of a somatotrophin releasing-factor.

2. The method of claim 1 wherein the somatotrophin releasing-factor is GRF-29, GRF-37, GRF-40, GRF-44 or GRF-NH$_2$-44.

3. The method of claim 2 wherein the somatotrophin releasing-factor is GRF-29.

4. The method of claims 1, 2 or 3 additionally comprising administering to said patient a pharmacologically efficacious quantity of follicle stimulating hormone.

5. The method of claim 4 wherein said follicle stimulating hormone is administered as menotrophin or urofollitrophin.

6. The method of claim 4 wherein said follicle stimulating hormone is administered simultaneously, sequentially or separately with said somatotrophin releasing-factor.

7. A method of stimulating follicle growth and maturation followed by ovulation in a female patient comprising administering to said patient during the first phase of the menstrual cycle a pharmacologically efficacious quantity of a somatotrophin releasing-factor.

8. The method of claim 7 wherein the somatotrophin releasing-factor is GRF-29, GRF-37, GRF-40, GRF-44 or GRF-NH$_2$-44.

9. The method of claim 8 wherein the somatotrophin releasing-factor is administered during the first seven days of the menstrual cycle.

10. The method of claim 8 wherein the somatotrophin releasing-factor is administered at about 100–150 mcg/day.

11. The method of claims 8, 9 or 10 additionally comprising administering to said patient a pharmacologically efficacious quantity of follicle stimulating hormone.

12. The method of claim 10 wherein the follicle stimulating hormone is administered at about 75–150 I.U./day during the first seven days of the menstrual cycle.

13. A method of treating spermatogenesis deficiency in a male patient comprising administering to said patient a pharmacologically efficacious quantity of a somatotrophin releasing-factor.

14. The method of claim 13 wherein the somatotrophin releasing-factor is GRF-29, GRF-37, GRF-40, GRF-44 or GRF-NH$_2$-44.

15. The method of claim 14 wherein the somatotrophin releasing-factor is administered at about 5 mcg/kg s.c. three times per week.

16. A pharmaceutical composition comprising about 100 to 150 mcg quantities of a somatotrophin releasing-factor and follicle stimulating hormone with one or more pharmaceutically acceptable excipients about 75 to 150.

17. The pharmaceutical composition of claim 16 wherein said somatotrophin releasing-factor is GRF-29, GRF-37, GRF-40, GRF-44 or GRF-NH$_2$-44.

18. The pharmaceutical composition of claim 17 wherein said somatotrophin releasing-factor is GRF-29.

19. The pharmaceutical composition of claim 18 wherein said follicle stimulating hormone is in the form of menotrophin or urofollitrophin.

* * * * *

UNITED STATES PATENT AND TRADEMARK OFFICE
CERTIFICATE OF CORRECTION

PATENT NO. : 5,017,557

DATED : May 21, 1991

INVENTOR(S) : Andrea Fabbri et al

It is certified that error appears in the above-identified patent and that said Letters Patent is hereby corrected as shown below:

In column 16, line 65, delete "quantities"; line 66, before "follicle" insert --about 75 to 150 IU of--; and line 67-68, delete "about 75 to 150".

Signed and Sealed this

Twenty-second Day of September, 1992

Attest:

DOUGLAS B. COMER

*Attesting Officer*  *Acting Commissioner of Patents and Trademarks*